United States Patent [19]

Fischer et al.

[11] 4,313,736
[45] Feb. 2, 1982

[54] FIELD TEST FOR METHAQUALONE AND MECLOQUALONE

[76] Inventors: John F. Fischer, 2409 Oberlin Ave., Orlando, Fla. 32804; Wayne A. Morris, 400 S. Edgemon, Winter Springs, Fla. 32708

[21] Appl. No.: 214,128

[22] Filed: Dec. 8, 1980

[51] Int. Cl.$^3$ .................. G01N 31/22; G01N 33/15
[52] U.S. Cl. ............................. 23/230 M; 23/910
[58] Field of Search ................ 23/230 B, 910, 230 M

[56] References Cited
PUBLICATIONS

Sanghavi et al., Chem. Abstracts, vol. 85, 1976, 85:37326s
Siple et al., Chem. Abstracts, vol. 85, 1976, 85:41664t.
Demme et al., Chem. Abstracts, vol. 88, 1978, 88:31805n.
Pai, Chem. Abstracts, vol. 88, 1978, 88:197742q.
Kar et al., Chem. Abstracts, vol. 92, 1980, 92:28680v.

*Primary Examiner*—Arnold Turk
*Attorney, Agent, or Firm*—Duckworth, Allen, Dyer & Pettis

[57] ABSTRACT

A method for indicating the presence of methaqualone and/or mecloqualone is disclosed comprising the steps of adding seven drops of 85% solution of formic acid to the substance suspected of containing methaqualone or mecloqualone. Thereafter, adding five drops of five percent aqueous solution of sodium nitrite, and six to ten drops of chloroform. A positive indication of the presence of methaqualone or mecloqualone results in a yellow color in the chloroform and a clear water-white color in the aqueous solution.

6 Claims, No Drawings

FIELD TEST FOR METHAQUALONE AND MECLOQUALONE

BACKGROUND OF THE INVENTION

The present invention is directed to the field of drug testing generally and more specifically to a color test for methaqualone and mecloqualone which may be easily performed by a police officer.

Drug abuse has become a growing problem in this country, with many pharmaceutical substances being abused by drug users. One of those substances which is now popularly abused is methaqualone which is also known by the trademarked name Quaaludes, and in street terminology, "'ludes". Recently numerous tablets appearing to be Quaaludes (Lemmon 714, or Rorer 714) have been seized by narcotic agents and have been found to contain substances other than methaqualone. Diazepam (valium) or diphenhydramine (benadryl) are most commonly encountered. In some cases these tablets have been found to contain little or no methaqualone. This has presented a serious problem for drug enforcement officials which may have no idea as to the content of tablets which they are "buying" in order to make drug arrests. This in turn has led to increasing difficulties in establishing probable cause for arrest and for search warrants.

Color tests for the detection of organic compounds are quite old in the art. Hugo Schiff developed a color spot test as early as 1859 for uric acid. Spot test did not become a matter of attention until around 1920. Since that time, the use of spot tests as a means for indicating a possible class of compounds being present has become, and still is becoming an ever widening field.

Numerous spot tests have been developed over the last one hundred years for the indication and/or identification of various drugs. Not until fairly recently, however, has their necessity ventured into the field of criminal justice, as related to law enforcement and forensic science. Today, with an ever widening horizon of new pharmaceutical compounds, as well as illicit drugs, the field of color testing as applied to forensic science and the criminal justice system has had a tendency to lag behind.

A color test has been developed for the indication of cannabinoids. A reagent, usually ethanol, vanillin, and acetaldehyde, is added to the test material, after which a second reagent, usually concentrated hydrocholoric acid, is added to the test solution. Should cannabinoids be present a blue-purple will develop. Upon the development of the color complex, chloroform is added, and the test solution is shaken. If cannabinoids are present the color will extract in the lower chloroform layer. This test for cannabinoids is called the Duquenois-Levine color test. The Duquenois-Levine color test is chemically based on the presence of the 1, 3-dioxybenzene (resorcinal) partial structure. It appears that the reaction proceeds via electrophilic substitution of the aromatic ring of the substrate by the protonated aldehydic group of vanillin or acetaldehyde or both. The Duquenois-Levine color test is considered positive if a purple color is extracted.

A number of other tests exist such as the Van Slyke, Liebermans, and Millon's. The use of nitrous acid in determining the number of free amine groups in amino acids was developed by Van Slyke. In this test, the nitrogen gas liberated was measured.

The Lieberman test uses sodium or potassium nitrite in concentrated sulfuric acid. This test is generally used to test for phenols. The reaction is based on the conversion of a portion of the phenol into p-nitrosophenol, by the action of nitrous acid, and condensation of the resulting nitrosophenol with the unchanged phenol which leads to the production of a colored indophenol. The Lieberman test was tested for color indication of methaqualone but was found inferior to the present invention in that it gave a positive indication on a much larger number of substances. In the Millon test, the reaction is the probable formation of a nitro compound, which then reacts with phenol. The test procedure, reagents, and chemistry are essentially dissimilar from the test of the present invention.

Another color test uses sodium cobaltinitrite to detect o-nitrosophenols. The brown cobaltic chelate is extracted into chloroform. Acetic acid is used as the solvent for the reaction. The present invention differs in that the nitrososation of methaqualone (or mecloqualone) is the final product formation step and thus the chloroform extract is more of a discerning step than in the cobaltic chelate reaction.

The present commercially available methaqualone test is made by Becton & Dickinson and consists of a two step procedure. It utilizes two ampules in a plastic bag. After the unknown powder is placed in the bag, it is sealed, and a first ampule containing a pink solution is broken. A second ampule containing a water-white liquid is then broken, (the second ampule probably is a dilute sulfuric acid solution). A blue solution or blue specks in a pink solution gives a positive result. When tested on a pharmaceutical Quaalude tablet, the results were not the definitive colors expected for a positive indication. Several attempts resulted in one indefinite positive, several questionable results, and several negatives. These results agree with comments from several police officers who have used the Becton & Dickinson test and found it inadequate.

SUMMARY OF THE INVENTION

In order to overcome the deficiencies of the prior art tests a color test for the indication of methaqualone has been devised comprising the steps of placing scrapings from the interior of a suspected methaqualone tablet into a micro test tube; adding seven drops of concentrated formic acid; thereafter adding five drops of a five percent sodium nitrite/water solution. The liquids are then mixed and a brown vapor is given off. If methaqualone is present a bright yellow solution develops. Thereafter, chloroform is added and if methaqualone is present a yellow extract is observed in the lower chloroform layer, and no color in the upper layer.

DESCRIPTION OF THE PREFERRED EMBODIMENT

As developed above, there is a need for a color test for the indication of the presence of methaqualone or mecloqualone in tablets purchased by drug enforcement officials. The following test has proven to be quite adequate. First, the tablet suspected of containing methaqualone or mecloqualone is broken in half and scrapings from the interior are placed into a micro-test tube. Concentrated formic acid is then added. A number of other acids have been tried with less than desirable results. These acids have included organic acids with similar pK values, organic acids with similar structures, and different dilutions of mineral acids. No positive tests were observed for methaqualone in any of these cases with the exception of nitrous acid which gave a very slowly developing positive test. Subsequently, a sodium nitrite/water solution is added. Sodium nitrite was chosen for its ready availability, but any soluble salt of the nitrite anion may be substituted. Furthermore, the actual intermediate is unknown but is formed in the equilibrium of nitrous acid as shown below.

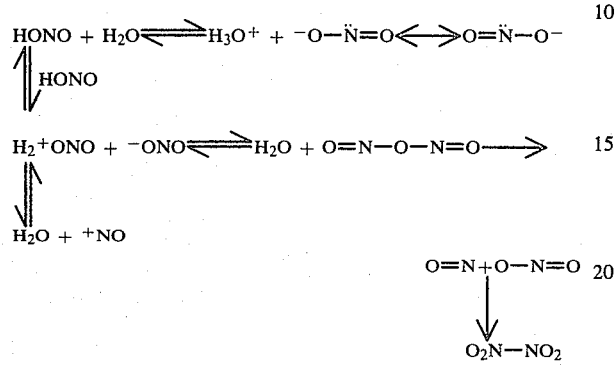

The combination is then mixed, whereupon a brown vapor is given off. It is believed that the brown vapor is nitrogen dioxide which is highly corrosive. If methaqualone is present, a bright yellow solution develops. The yellow color is a preliminary indication of the presence of methaqualone, however, it is not a sufficiently discriminative indication since diphenhydramine, which is found in combination with methaqualone in a European commercial tablet and in some counterfeit tablets, also gives a yellow solution as will several other substances. For this reason, an extraction is performed. This is done by adding a quantity of chloroform or other non-polar organic liquid to the solution. After the addition of the chloroform, if methaqualone is present, a yellow extract is observed in the lower chloroform layer and no color is observed in the upper layer. The upper layer will be water-white.

Two factors determine whether a result will be considered positive. First, nitrosomanines are yellow, therefore, if a nitrosomanine is formed, the yellow solution should result. Secondly, solubility in chloroform of the colored product results in a yellow chloroform layer. It is the second factor which reduces the number of false positivites to a level which becomes extremely useful.

Some primary amines may be converted into nitrosomanines. However, the majority of primary amines will continue to a carbonium ion and free nitrogen. This is the basis for Van Slyke's test. Tertiary amines may give either salts, or via a complex reaction, a nitroso derivitives of secondary amines. Thus for the most part, only secondary amines will react to give a potential false positive, and not all of these reaction products will be soluble in chloroform.

The proposed test discriminates against many of the substances used in "counterfeit Quaaludes". A common preparation of "counterfeit Quaaludes" is one containing diazepam. Diazepam will give a yellow solution after the addition of sodium nitrite, but no color will be extracted by the chloroform.

In performing the test it is suggested that a sample scraping be taken from an internal portion of the tablet rather than the outer portion due to the fact that some substances which might have come in contact with the tablet may cause misleading results. The optimum conditions for this test were determined to be the use of seven drops of formic acid (85%) to five drops of sodium nitrite (5% aqueous solution), and six to ten drops of chloroform. The yellow colors indicated in the test are brilliant under these conditions. The scrapings of tablets, or the amount of powder needed for a highly definitive color result was less than 0.3 mg. Although this test uses sodium nitrite, nitrous acid or any of its equilibrium products may be used. Sodium nitrite was chosen for its ease of handling, chemical stability in solution, and chemical safety. Formic acid was found to be the best acidic medium over any other acids which may be used for this test. Several acids in concentrated solution were found to form color complexes upon combining with the sodium nitrite, while other acids under room temperature conditions (concentrated and dilute) gave no appreciable reaction. Other acids gave results between the extremes with formic acid giving the best results.

The stated drop ratio of seven to five for the formic acid and sodium nitrite solutions has been found to give the best results. Although the positive result for methaqualone is obtained for a wide range of ratios, diazepam is best discriminated at the ratio of seven to five. The order of addition and the ratio of seven to five is the route which discriminates the most substances, including diazepam and diphenhydramine, from methaqualone and mecloqualone.

In the case of coincidental reactions which result in a yellow product, very few should give a yellow product which is soluble in chloroform.

The following results were determined by the application of the method disclosed to numerous substances some of which are used in counterfeit Quaaludes. Note that in the table, A is the reaction after the addition of formic acid; B is the reaction after the addition of sodium nitrite; C—up is the color in the upper layer after the addition of chloroform; and C-lower is the color in the lower layer after the chloroform was added.

| DRUG | A | B | C up | C lower |
|---|---|---|---|---|
| Cocaine | — | pale-green | pale-green | pale-green |
| Methaqualone | — | yellow | clear | yellow |
| Mecloqualone | — | yellow | clear | yellow |
| Diazepam | pale yellow | yellow | yellow | clear |
| Procaine HCl | — | pale blue | clear | tinged |
| Caffeine | — | pale blue | tinged | tinged |
| PCP HCl | — | pale blue-green | tinged | tinged |
| Aspirin | | yellow-green | yellow-green | yellow |
| APC | — | large foaming yellow | yellow | yellow |
| Vitamin B$_{12}$ | — | large foaming tinged yellow | clear | tinged |
| Benzoic Acid | yellow | green/yellow green | yellow | yellow |
| Butacaine HCl | honey | yellow | yellow | yellow |
| Carisoprodol | — | blue-green yellow-green | clear | yellow |
| Meprobamate | yellow | honey | honey | yellow |
| Chlorzoxazone | — | bright yellow | yellow | lemon-yellow |
| Chlorphennamine | — | pale blue-green | pale green | clear |
| Methaqualone/ Diphenhydramine | — | yellow or pale-green | pale yellow | yellow |
| Phenobarbital | — | yellow | yellow | clear |
| Diphenhydramine | — | yellow | pale | clear |

-continued

| DRUG | A | B | C up | C lower |
|------|---|---|------|---------|
|      |   |   | yellow |       |

By performing numerous experiments using different ratios of formic acid and sodium nitrite it was found that a ratio of anywhere from 20 to 1 to 83 to 1 (by weight) of formic acid to sodium nitrite resulted in an indication of the presence of methaqualone and mecloqualone. However, the preferred embodiment described above which is a ratio of 23.8 to 1 by weight of formic acid to sodium nitrite was best able to discriminate against diazepam which is a common ingredient of fake Quaaludes.

I claim:

1. A method of indicating the presence of methaqualone or mecloqualone comprising the steps of:
    adding a quantity of a formic acid solution of predetermined concentration to the sample;
    adding a quantity of sodium nitrite solution, so that the ratio of formic acid to sodium nitrite is between 20 to 1 and 83 to 1 by weight;
    adding a quantity of non-polar organic liquid sufficient to form two distinct layers, one of which primarily consists of the non-polar organic liquid; and
    visually detecting a yellow color which is extracted in the non-polar organic liquid layer.

2. The method of claim 1 wherein the ratio of formic acid to sodium nitrite is 23.8 to 1 by weight.

3. The method of claim 1 wherein the non-polar organic liquid is chloroform.

4. The method of claim 2 wherein said step of adding a quantity of a formic acid solution comprises adding seven drops of an 85% formic acid solution and wherein said step of adding a quantity of sodium nitrite comprises adding five drops of a 5% sodium nitrite solution.

5. The method of claim 4 wherein said step of adding a quantity of non-polar organic liquid comprises adding between six to ten drops of chloroform.

6. A method of discriminating between the presence of methaqualone or mecloqualone from the presence of diazepam, in a sample comprising the steps of:
    adding seven drops of an eighty-five percent (85%) solution of formic acid and solution to the sample;
    adding five drops of a five percent (5%) solution of sodium nitrite;
    adding between six to ten drops of chloroform to form a chloroform layer; and
    visually detecting the presence of yellow coloring in the chloroform layer.

* * * * *